(12) United States Patent
Thiel et al.

(10) Patent No.: US 10,561,450 B2
(45) Date of Patent: Feb. 18, 2020

(54) BONE PLATE AND SURGICAL KIT FOR FIXING BONE FRAGMENTS

(71) Applicant: MEDARTIS HOLDING AG, Basel (CH)

(72) Inventors: Dirk Thiel, Staufen (DE); Alexander Zuberer, Kandern (DE)

(73) Assignee: MEDARTIS HOLDING AG, Basel (CH)

( * ) Notice: Subject to any disclaimer, the term of this patent is extended or adjusted under 35 U.S.C. 154(b) by 226 days.

(21) Appl. No.: 15/546,351

(22) PCT Filed: Feb. 26, 2015

(86) PCT No.: PCT/EP2015/054055
§ 371 (c)(1),
(2) Date: Jul. 26, 2017

(87) PCT Pub. No.: WO2016/134775
PCT Pub. Date: Sep. 1, 2016

(65) Prior Publication Data
US 2018/0021071 A1  Jan. 25, 2018

(51) Int. Cl.
*A61B 17/80* (2006.01)
*A61B 17/86* (2006.01)

(52) U.S. Cl.
CPC ...... *A61B 17/8014* (2013.01); *A61B 17/8052* (2013.01); *A61B 17/8605* (2013.01)

(58) Field of Classification Search
CPC ........... A61B 17/8014; A61B 17/8009; A61B 17/8052
See application file for complete search history.

(56) References Cited

U.S. PATENT DOCUMENTS 3,528,085 A  *  9/1970  Reynolds, Jr. ..... A61B 17/8014
                                        52/848
6,572,622 B1    6/2003  Schäfer et al.
(Continued)

FOREIGN PATENT DOCUMENTS

DE   10 2010 025 000 A1   12/2011
EP      1 093 762 A2       4/2001
(Continued)

OTHER PUBLICATIONS

Translation of FR-1505513-A from EPO website (Year: 2019).*
(Continued)

*Primary Examiner* — Christian A Sevilla
(74) *Attorney, Agent, or Firm* — Davis & Bujold PLLC; Michael J. Bujold

(57) ABSTRACT

A bone plate (1) with at least one receiving opening (2) for a bone screw (3) with a screw head (4), wherein the receiving opening (2) has a compression area (5) with a compression contour (6) and a blocking area (7) with a blocking contour (8). The compression contour is designed such that rotation of the bone screw in its one screwing-in direction (E) causes lateral movement of the bone screw toward the blocking area (7). The compression contour (6) is designed as an engagement contour (6), such that lateral movement is generated by engagement between the engagement contour (6) and a mating contour (9) on the screw head or tool. A surgical kit containing at least one such bone plate (1) and at least one bone screw with a screw head (4), which bone screw is insertable into the receiving openings of the bone plate (1) is also disclosed.

19 Claims, 10 Drawing Sheets

(56) References Cited

U.S. PATENT DOCUMENTS

Figure 1B:
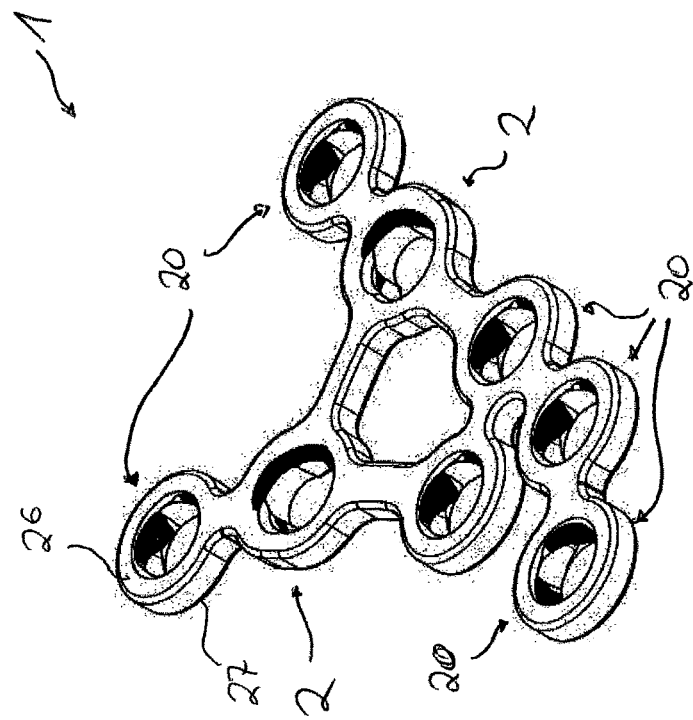

| | | | |
|---|---|---|---|
| 6,730,091 | B1 | 5/2004 | Pfefferle et al. |
| 7,354,441 | B2 | 4/2008 | Frigg |
| 8,940,026 | B2 | 1/2015 | Hilse et al. |
| 9,155,577 | B2 | 10/2015 | Pfefferle et al. |
| 9,271,769 | B2 | 3/2016 | Batsch et al. |
| 2002/0183755 | A1* | 12/2002 | Michelson ......... A61B 17/7059 606/71 |
| 2008/0015592 | A1 | 1/2008 | Long et al. |
| 2009/0234359 | A1 | 9/2009 | Onoue et al. |
| 2009/0264934 | A1 | 10/2009 | Youssef et al. |
| 2012/0197303 | A1 | 8/2012 | King et al. |
| 2012/0197307 | A1 | 8/2012 | Fritzinger et al. |

FOREIGN PATENT DOCUMENTS

| | | | |
|---|---|---|---|
| EP | 2 364 658 A1 | 9/2011 | |
| FR | 1505513 A * | 12/1967 | ......... A61B 17/8014 |
| WO | 00/66012 A1 | 11/2000 | |
| WO | 2004/086990 A1 | 10/2004 | |
| WO | 2010/115403 A1 | 10/2010 | |
| WO | 2011/160846 A1 | 12/2011 | |
| WO | 2012/000627 A1 | 1/2012 | |
| WO | 2014/033088 A1 | 3/2014 | |

OTHER PUBLICATIONS

International Search Report Corresponding to PCT/EP2015/054055 dated Nov. 23, 2015.
Written Opinion Corresponding to PCT/EP2015/054055 dated Nov. 23, 2015.

* cited by examiner

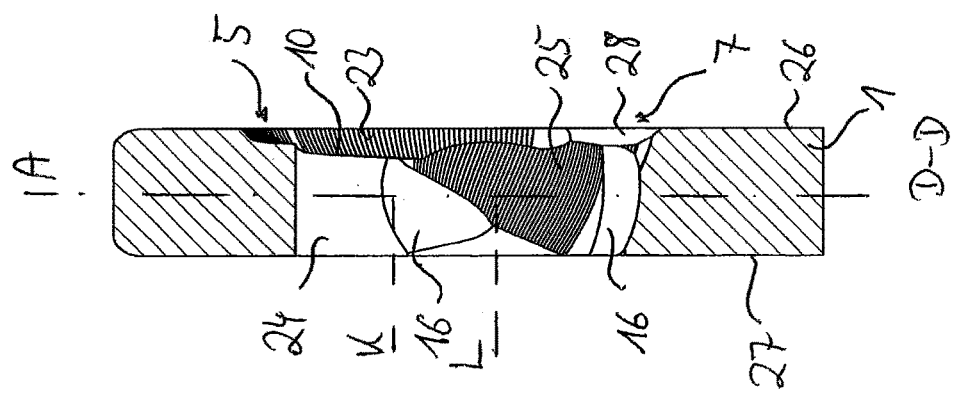
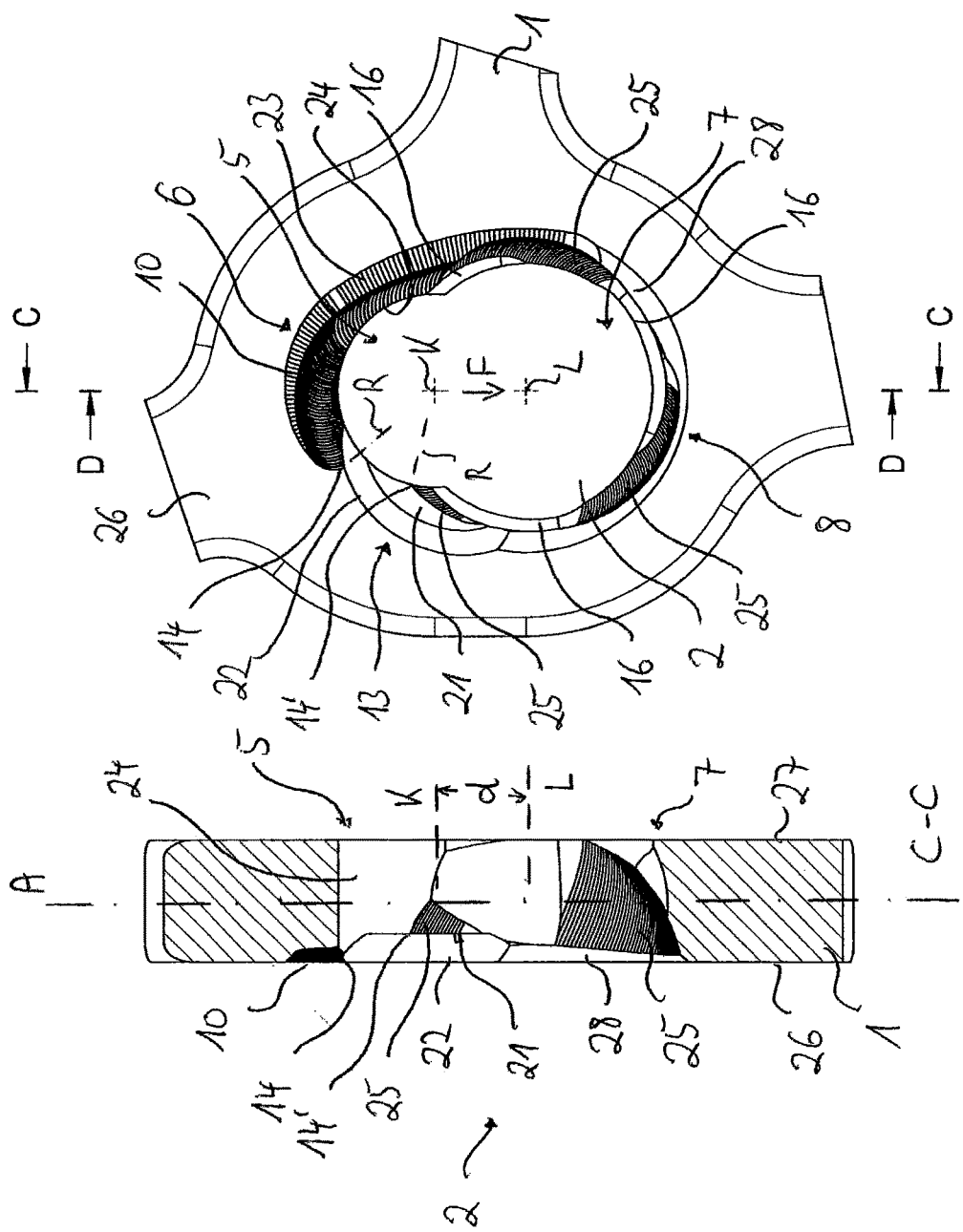
FIG. 3c
FIG. 3a
FIG. 3b

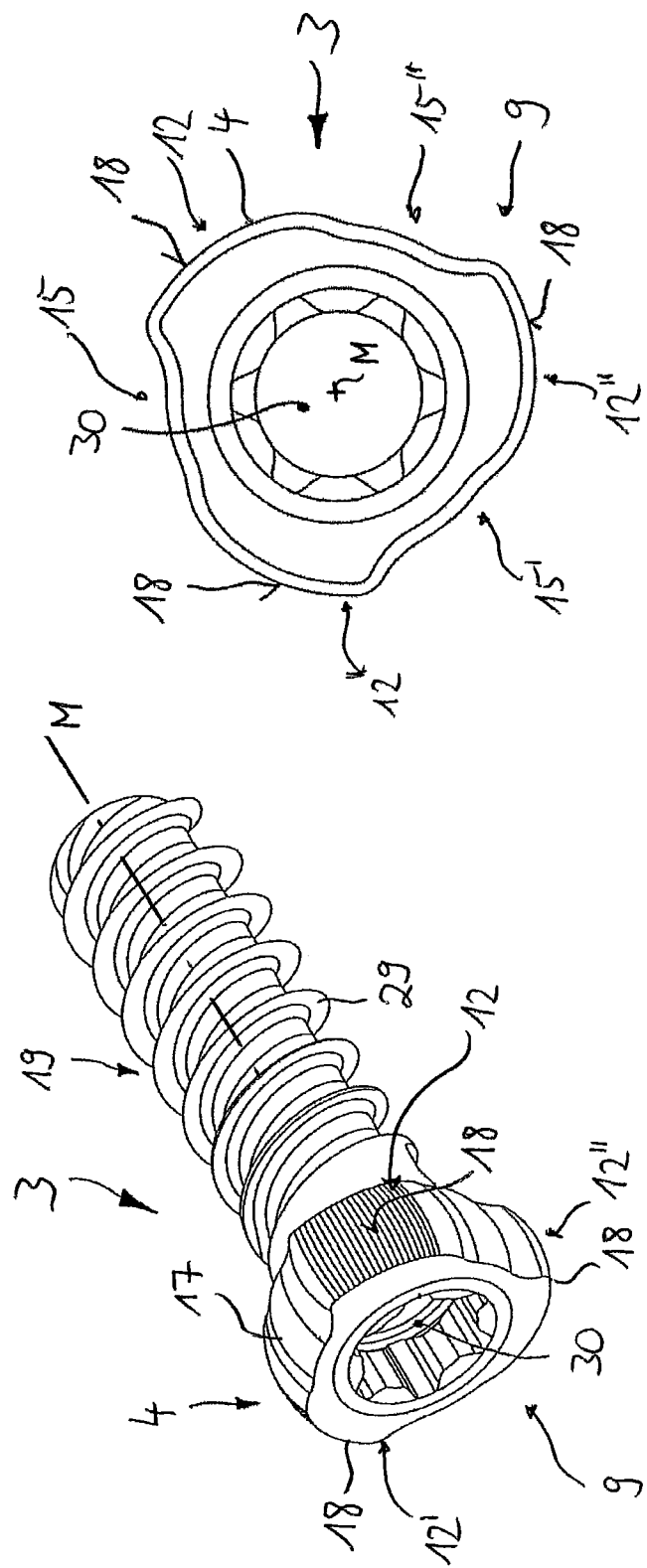

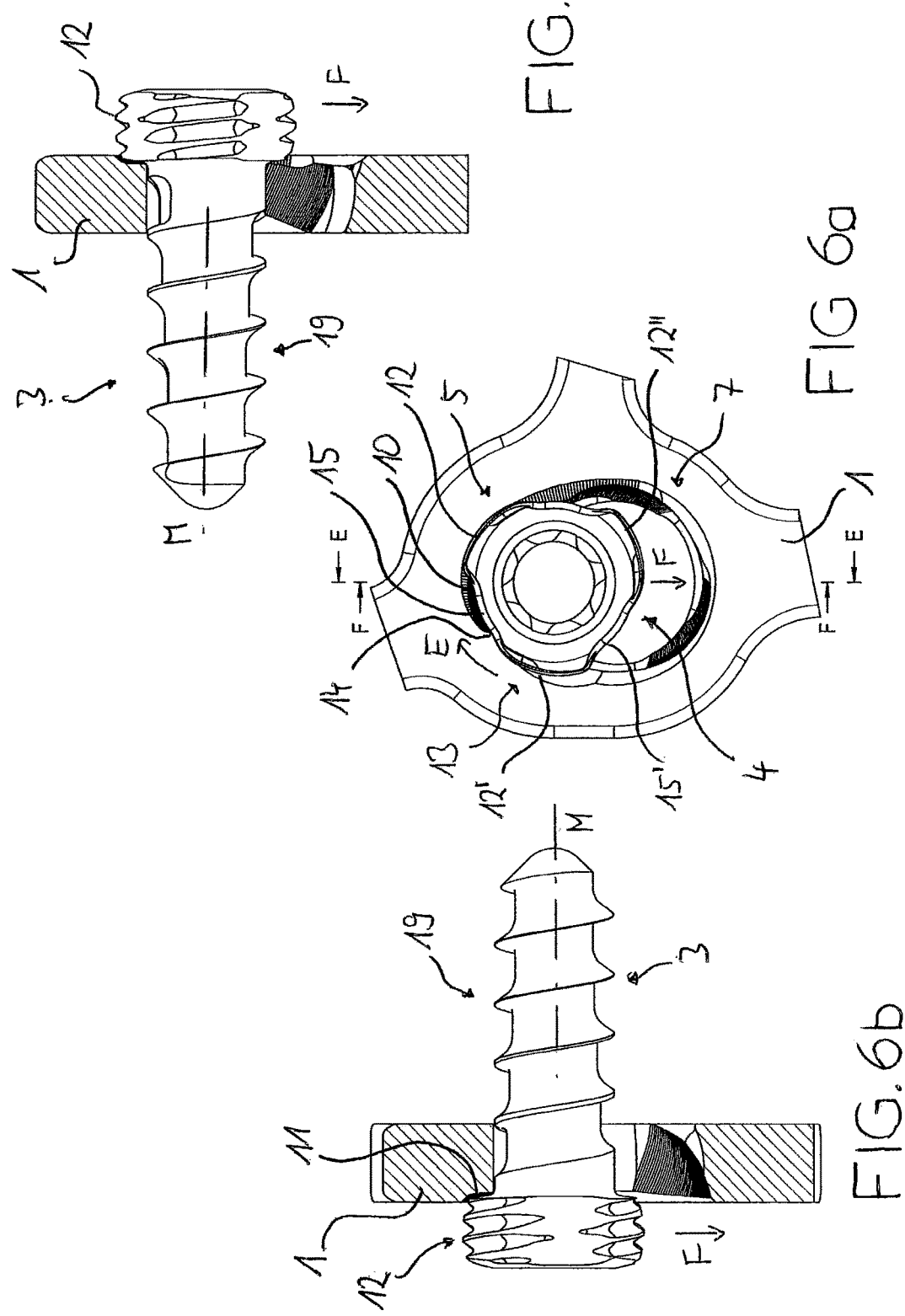

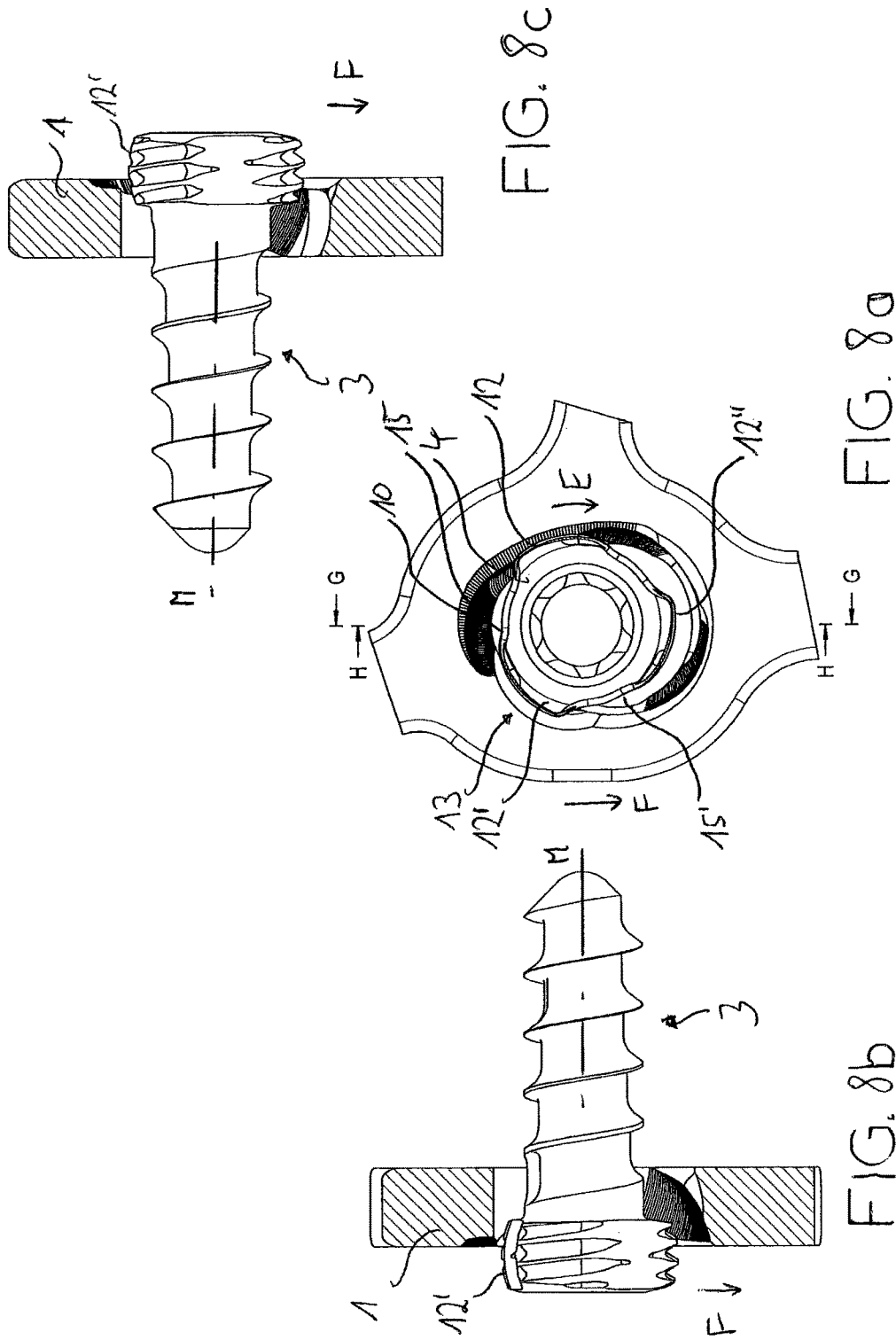

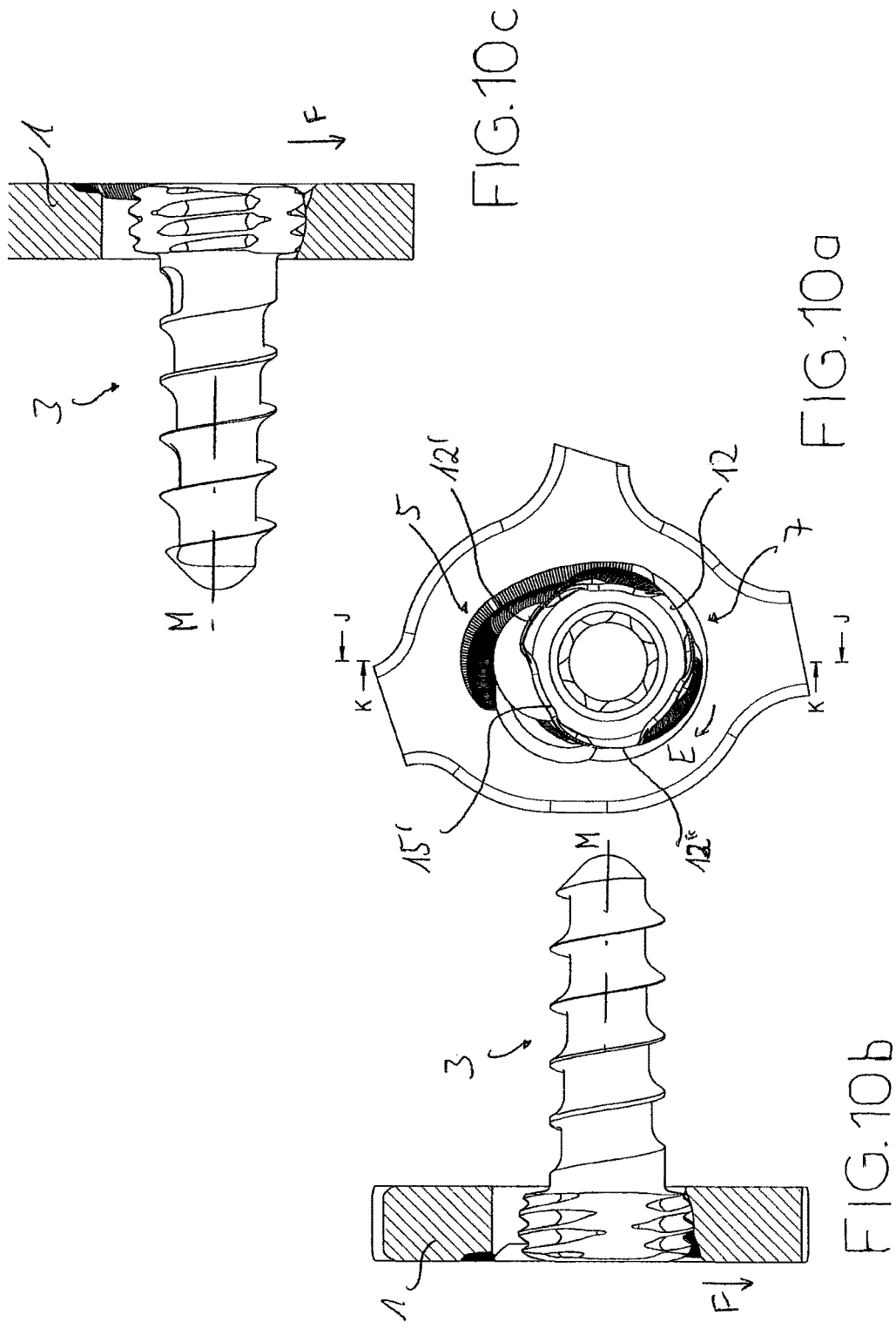

BONE PLATE AND SURGICAL KIT FOR FIXING BONE FRAGMENTS

The present invention relates to bone plates, surgical kits and methods for fixing a bone plate.

To heal bone fractures using bone plates, two functions are particularly important, namely compression and blocking.

During the compression, two bone fragments are moved toward one another along a compression path such that a fracture gap formed between said bone fragments is closed. Such compression per se can be achieved with especially designed compression holes which are disclosed in the prior art and are realized in such a manner that an axial movement of a bone screw, directed into the bone, is converted into a lateral movement of the bone screw. To this end, the known bone plates include compression holes with a compression contour which comprise, for example, a sliding surface which is angled in relation to the plate plane.

The known bone plates are initially fastened by means of a first bone screw to a first of the two bone fragments. A second bone screw is then inserted through the compression hole into a second of the two bone fragments. When the second bone screws are tightened, the bottom surface of the screw head slides down the sliding surface, which brings about a relative movement between the second bone screw and the bone plate and consequently between the two bone fragments, that is to say compression.

Blocking, which is equally known per se, is to be understood as the fixing of a head of the bone screw in the bone plate. As a result, a bone plate can be fastened to a bone in an angularly stable manner. In this case, it is enormously advantageous when the bone screw can be fastened to the bone plate at a variable angle in order to be able to support the individual anatomy of the patient being treated.

U.S. Pat. No. 7,354,441 B2 discloses a combination hole with a first, substantially circular region and a second, elongated region. The first region has a thread. On account of the contour of the combination hole, the bone fragments to be joined are compressed when a bone screw is tightened.

WO 00/66012 A1 discloses blockable bone plates. In one exemplary embodiment, compression osteosynthesis is shown. By screwing bone screws into a compression hole, the bone fragments are moved toward one another such that a fracture gap formed between them closes.

US 2008/0015592 A1 is concerned with variably usable holes: as an option, a compression screw can be inserted in order to bring about compression, or a blocking screw can be inserted in order to achieve blocking. For this purpose, the holes have compression surfaces and specially formed curved paths. A bone screw, which has cams which are guided along the curved paths, is used for blocking. A bone screw without cams is used for compression. The head thereof slides down the compression surface when the screw is tightened.

WO 2010/115403 A1 is concerned with the angularly stable fixation and compression of a fracture point, both functions having to be achieved at the same time with one single bone screw. For this purpose, the bone plate has a fixation and compression hole which is formed from two circular holes which comprise different diameters. In this way, a crescent-shaped widening is generated. A fine thread is provided in the hole. When the bone screw is screwed in, an external thread of said bone screw penetrates laterally into the open part of the internal thread and engages the same such that in the screwed-in state, the thread head is completely received in the internal thread.

The holes of the bone plates disclosed in EP 2 364 658 A1 include a first region, a second region and a transition region. The transition region, in this case, is realized such that a lateral movement between plate and screw is possible. To this end, the transition region includes a beveling which results in compression.

WO 2011/160846 A1 discloses bone plates with two differently sized, intersecting, stepped round holes, in the upper regions of which extends a circumferential rib. The bone plates according to the invention are to be able to be applied with different kinds of bone screws (with cone seats or ball seats). A bone screw with thread on the screw head can be supported on the rib of the smaller round hole and enable engagement for the rib of the larger round hole, as a result of which there is reciprocal clamping.

The very similar DE 10 2010 025 000 A1 also discloses bone plates with two differently sized, intersecting, stepped round holes as well as a radial rib.

WO 2012/000627 A1 also discloses a bone plate with two differently sized, intersecting, stepped round holes, in the upper regions of which extends a rib.

US 2012/0197307 A1 also discloses a combined screw hole for blocking and compressing.

WO 2004/086990 A1 discloses receiving openings for bone plates which allow the bone screws to be blocked at different angles relative to the bone plate. Some embodiments have an elongated hole with a blocking contour which can be used for compression osteosynthesis.

However, the concept utilized in the case of all said bone plates, of the bottom surface of the screw head sliding down a sliding surface of the compression hole, comprises a series of disadvantages. For if the angle between the sliding surface and the plate plane is chosen to be too flat, large forces have to be applied in the screwing-in direction in order to be able to bring about any lateral movement whatsoever of the bone screw relative to the bone plate and consequently to bring about compression. Said large forces in the screwing-in direction can, however, already result in unnecessary damage to the screw head, the bone plate or even the bone. In addition, on account of the large necessary forces, there is the risk of the tool used for screwing-in inadvertently slipping off. In other words, there is therefore unfavorable force transmission between the force acting in the screwing-in direction and the force producing the lateral movement. If, in contrast, the angle between the sliding surface and the plate plane is chosen to be too steep, the plate, with the compression path being a predetermined length, has to be realized in a correspondingly thicker manner at least in the region of the compression hole. This results not only in increased material requirement, but can also add unnecessary damage to the surrounding body tissue.

In addition, the compression holes disclosed in U.S. Pat. No. 7,354,441 B2, WO 00/66012 A1, WO 2010/115403 A1 and EP 2 364 658 A1 certainly comprise threads which enable a correspondingly realized screw head to be blocked. However, such types of threads provide one single blocking direction in which the bone screw can be blocked exclusively; blocking at different angles relative to the bone plate is therefore not possible.

To obtain compression, further mechanisms are also disclosed in the prior art, which, however, do not allow blocking or comprise further disadvantages:

Thus, WO 2014/033088 A1 discloses a two-part bone plate with a main body and a movable part. The movable part has a toothed rod. As a result of rotating a toothed wheel, it can interact with the toothed rod in such a manner that the two parts are displaced relative to one another, as a result of which compression can be achieved. However, screwing-in a bone screw does not automatically result in compression of the bone fragments to be joined. In addition, blocking cannot be achieved directly, let alone one at different angles relative to the bone plate.

US 2012/0197303 A1 is concerned with bone plates with elongated holes, on the one side of which a toothed rod is arranged. A pinion shaft arrangement can be inserted into such an elongated hole. When a threaded end of the pinion shaft arrangement is screwed into a bone, compression is effected as a result of interaction between the pinion and the toothed rod. However, the screw openings of said bone plates do not include any contours which enable both compression and blocking, let alone blocking at different angles relative to the bone plate.

US 2009/0234359 A1 discloses a bone plate with an elongated hole which has a toothed rod. A pinion can be inserted into said elongated hole, compression can be produced as a result of rotating said pinion. As in the case of US 2012/0197303 A1, however, there are not any screw openings with contours present here either which enable both compression and blocking, let alone blocking at different angles relative to the bone plate.

It is consequently an object of the present invention to provide a bone plate which does not comprise the above-explained disadvantages of the prior art. In particular, the bone plate is to comprise at least one receiving opening for a bone screw which allows both compression and blocking. In this case, during compression, as favorable as possible a force transmission is to be obtained without the bone plate having to comprise an excessive thickness in the region of the receiving opening just for this purpose. In a preferred manner, the receiving opening is to allow blocking at different angles relative to the bone plate.

These and further objects are achieved, on the one hand, by a bone plate according to the invention. Said bone plate comprises at least one receiving opening for a bone screw with a screw head. The receiving opening includes a compression region with a compression contour and a blocking region with a blocking contour. The compression contour is realized and arranged in such a manner that rotation of the bone screw in a screwing-in direction brings about a lateral movement of the bone screw in the direction of the blocking region.

According to the invention, the compression contour is realized as an engagement contour such that the lateral movement is generatable at least in part, in particular completely, by an engagement between the engagement contour and a counter contour on the screw head.

The lateral movement being generatable "at least in part" by an engagement between the engagement contour and a counter contour on the screw head means in this connection that said engagement is present during at least part of the compression operation. This does not exclude, therefore, any such engagement being present during another part of the compression operation or the lateral movement not being generated in any case as a result thereof.

In contrast to the prior art, the lateral movement is therefore not generated exclusively by the bottom surface of the screw head sliding down a sliding surface of the compression contour which is produced by the axial movement of the bone screw. Instead, the rotation of the bone screw in its screwing-in direction provides for said lateral movement at least in part or even completely as a result of an engagement between the engagement contour and the counter contour. An advantageous force transmission can be obtained in this way without the bone plate having to comprise an excessive thickness in the region of the receiving opening for this purpose.

In particular, in individual embodiments, the sliding surfaces which are disclosed in the prior art and are angled relative to the plate plane can be dispensed with completely. The thickness of the bone plate in the region of the receiving opening is not determined solely by the gradient of such a sliding surface in relation to the plate plane nor by the length of the compression path.

Both the compression region and the blocking region can comprise a respective main axis. Such a main axis of the compression region has the characteristic of a bone screw being insertable into the compression region at least in such a manner that its longitudinal axis extends parallel to said main axis. It is conceivable for the bone screw to be insertable into the compression region additionally in such a manner that its longitudinal axis extends inside a solid angle area which includes the main axis of the compression region. In said case, the named main axis is not clearly defined, i.e. several axes which differ from one another can be understood as the main axis in terms of the above definition.

In an analogous manner to this, a main axis of the blocking region has the characteristic of a bone screw being insertable into the blocking region at least in such a manner that its longitudinal axis extends parallel to said main axis. It is conceivable for the bone screw to be insertable into the blocking region additionally in such a manner that its longitudinal axis extends inside a solid angle area which includes the main axis of the blocking region. In said case, the named main axis is not clearly defined, i.e. several axes which differ from one another can be understood as the main axis in terms of the above definition. The main axis of the compression region and the main axis of the blocking region can extend perpendicular to or at an angle to the plate plane independently of one another. The main axis of the compression region and the main axis of the blocking region can be at a distance apart from another which is within the range of between 0.2 mm and 5 mm, in a preferred manner of between 0.5 mm and 2 mm and in a particularly preferred manner of between 0.8 mm and 1.2 mm.

In an advantageous manner, the lateral movement is generatable at least in part, in particular completely, by rolling the screw head along part of the engagement contour, in particular along a rolling region which is described again further below. Rolling is to be understood here and below as the screw head rolling along part of the engagement contour, said rolling being able to be superimposed by sliding. Said rolling is effected, therefore, according to the principle of toothing between two toothed wheels or one toothed wheel and one toothed rod. Such rolling enables the screw head to be guided in a precise manner and reduces any material abrasion which might occur in the case of pure sliding. Pressing the bone screw onto the bone plate as a condition for the lateral movement is also unnecessary in practice. In addition, the movement can be effected along paths which have a theoretically unlimited length and/or are non-linear.

The lateral movement being generatable "at least in part" as a result of rolling means, in this connection, that the lateral movement is generatable as a result of rolling during at least part of the compression operation and/or rolling is only generatable between individual parts of the engagement contour and/or of the counter contour. Thus, it is conceivable, for example, and covered by the wording "at least in part", for the lateral movement not to be generatable by rolling during another part of the compression operation. Also covered by the wording "at least in part" is that a first part of the screw head is rolled along a first part of the engagement contour, whilst at the same time a second part of the screw head slides along a second part of the engagement contour.

In a preferred manner, the engagement contour comprises at least one guiding surface, along which, during the rotation of the bone screw in its screwing-in direction, a bottom surface of the screw head is guidable. Such guiding allows for more precise movement of the screw head. It can also contribute to generating the lateral movement, the lateral movement being generated according to the invention, however, at least in part also or even only by the engagement between the engagement contour and the counter contour. In addition, the named guiding provides that the screw head pulls the bone plate in the direction of the bone fragment into which it is screwed.

In a preferred manner, the guiding surface is realized in a cycloid-like manner. A cycloid-like realization is to be understood here and below as the guiding surface having such a characteristic which makes it possible for the bone screw, in particular a bottom surface of a blocking projection of the bone screw, to remain in contact with the guiding surface at least during part of the resultant movement, which results from the helical movement of the bone screw about its longitudinal axis and from the movement in the direction of the blocking region. As a result, the guiding surface can carry out the named resultant movement particularly well.

Equally in a preferred manner, the guiding surface is designed such that a bottom surface of a blocking projection, which is arranged radially on the screw head, is guidable along said guiding surface during rotation of the bone screw in its screwing-in direction. Such a blocking projection can serve for blocking the screw head on the blocking contour, as is described again in detail further below. The blocking projection can therefore provide the guiding of the screw head during compression and the subsequent blocking; it can therefore assume a dual function.

The guiding is effected in a preferred manner along a longitudinal axis of the bone screw, that is to say in the direction in which the bone screw is screwed into the bone.

The engagement contour can comprise at least one rolling region on which a blocking projection, which is arranged radially on the screw head, is rollable during at least part of the lateral movement.

The rolling region can include a bottom surface and a side surface, which extends between the top surface and the bottom surface, wherein the named blocking projection, which is arranged radially on the screw head, is rollable during at least part of the lateral movement on said side surface. The bottom surface can extend parallel to a top surface of the bone plate. As an alternative to this, however, it is also conceivable and is within the framework of the invention for the bottom surface to be realized in a cycloid-like manner in the above sense.

It is particularly advantageous for the blocking contour to be realized in such a manner that the bone screw is blockable at various angles relative to the bone plate. As has been explained above, the main axis of the blocking region does not necessarily have to be defined in a clear manner. The bone screw is therefore not only blockable in the blocking region in such a manner that its longitudinal axis extends parallel to one single possible main axis of the blocking region, but also in alignments which deviate therefrom. This has the advantage already explained above of the individual anatomy of the patient being treated being able to be taken into account.

The blocking region and in particular the blocking contour thereof can comprise one, several or all of the features disclosed in WO 2004/086990 A1. The disclosure in this respect in WO 2004/086990 A1 is hereby explicitly incorporated into the present application.

The blocking contour can comprise, in particular, at least one recess which widens outward in a wedge-shaped manner away from a main axis of the blocking region in order to be able to receive and block a blocking projection which is arranged radially on the screw head. Said wedge-shaped realization allows the screw head to be clamped in a radial manner, in particular by blocking projections which are arranged on the screw head, when the bone screw is rotated about its longitudinal axis.

In an advantageous manner, the blocking contour is realized in an at least approximately spherical, paraboloid, ellipsoid or hyperboloid manner at least in the region of the recess. In particular when the blocking contour is realized in an at least approximately spherical manner in the region of the recess, this enables the bone screw to be blocked at different angles relative to the bone plate.

Furthermore, the recess of the blocking contour is arranged in a preferred manner such that it extends around in a direction perpendicular to the main axis of the blocking region.

The blocking contour can comprise at least two, in a preferred manner at least three and in a particularly preferred manner precisely three recesses which widen outward in each case in a wedge-shaped manner away from the main axis of the blocking region. As a result, the screw head can be blocked in a particularly stable manner in the blocking contour. This applies, in particular, when the recesses extend uniformly in the circumferential direction around the main axis of the blocking region.

The blocking contour, in the region of the recess which widens outward in a wedge-shape manner away from the main axis of the blocking region, can be described in an azimuth plane which extends perpendicular to the main axis of the blocking region, by part of a logarithmic spiral, of a circular path, of an involute or of a root function of the type $r = a_1 + b_1\sqrt{\alpha}$, wherein r is the respective distance between the blocking contour and the main axis of the blocking region, $a_1$ and $b_1$ are constants and $\alpha$ stands for the respective circumferential angle.

The counter contour can be formed by at least one of the blocking projections and/or at least one of the recesses which are arranged between the blocking projections. The blocking projections and/or the recesses can then namely serve both for generating the lateral movement during compression and for the subsequent blocking; they can therefore assume a dual function.

In advantageous embodiments, a longitudinal axis of the bone screw extends along a straight path in the direction of the blocking region during the lateral movement. However, it is naturally also conceivable and is within the framework of the invention for said path to be curve-shaped at least in portions or even completely.

A further aspect of the invention relates to a surgical kit which includes at least one bone plate according to the invention as disclosed above and at least one bone screw with a screw head which is insertable into at least one of the receiving openings of the bone plate. In this way, the bone screw can be used together with the bone plate in the manner already explained in detail in order to bring about the equally explained advantages.

The bone screw can be a bone screw that is known per se, insofar as it comprises the above-described characteristics, in order to be able to interact in the described manner with the bone plate.

In a preferred manner, the bone screw comprises one, several or all of the features disclosed in WO 2004/086990 A1. The relevant disclosure of WO 2004/086990 A1 is also hereby explicitly incorporated into the present application.

In a preferred manner, the screw head with a blocking projection which is arranged radially on the screw head is provided with a circumferential outside surface which extends substantially in the direction of a longitudinal axis of the bone screw and comprises at least one clamping surface which, when viewed in an azimuth plane perpendicular to the longitudinal axis, widens outward in a wedge-shaped manner away from the longitudinal axis in order to be able to block the screw head with the blocking contour, in particular with the recesses thereof.

Also advantageously, the circumferential outside surface of the screw head is realized in an at least approximately spherical, paraboloid, ellipsoid or hyperboloid manner at least in the region of the clamping surface.

In addition, it is advantageous when the circumferential outside surface of the screw head comprises at least three, in a preferred manner precisely three clamping surfaces-which are distributed uniformly along their circumference and widen outward in each case in a wedge-shaped manner away from the longitudinal axis of the bone screw.

The contour of the outside surface of the screw head in the region of the clamping surface which widens outward in a wedge-shape manner away from the longitudinal axis can be described in an azimuth plane by part of a logarithmic spiral, by part of a circular path or by part of an involute or of a root function of the type $r = a_1 + b_1 \sqrt{\alpha}$, wherein r is the respective distance between the contour and the longitudinal axis, $a_1$ and $b_1$ are constants and $\alpha$ stands for the respective circumferential angle.

The blocking region can be provided with an, in particular, spherical countersink for receiving, for example, a screw head with a spherical head bottom surface.

If the bone screw includes a guiding surface as described above, it is matched in a preferred manner to the bone screw, in particular to a bottom surface of the screw head and to a thread pitch of a shank of the bone screw, in such a manner that the bottom surface of the screw head, in particular a bottom surface of a blocking projection which is arranged radially on the screw head, is guidable along the guiding surface, in particular along a longitudinal axis of the bone screw, during the screwing-in of the bone screw. The advantages of such guiding have already been pointed out above.

If at least one bone plate includes a rolling region as described above, said rolling region, in particular the side surface thereof, is matched in a preferred manner to the bone screw, in particular to a counter contour arranged on the screw head and to a thread pitch of a shank of the bone screw, in such a manner that the screw head is rollable on the rolling region, in particular on the side surface thereof, during the screwing-in of the bone screw.

A further aspect of the invention relates to a method for fixing a bone plate according to the invention as described above to two bone fragments to be joined. Said method includes the steps:
 a) fixing the bone plate to a first bone fragment by means of a first bone screw,
 b) inserting a second bone screw through the compression region of the receiving opening into a second bone fragment,
 c) rotating the second bone screws in a screwing-in direction, as a result of which a lateral movement of the second bone screw is brought about in the direction of the blocking region and the lateral movement is generated at least in part, in particular completely, by an engagement between the engagement contour and a counter contour on the screw head.

The above-explained advantageous structural characteristics of the bone plate according to the invention are therefore utilized in said method. The second bone screw can comprise one, several or all of the features described above in conjunction with the surgical kit according to the invention.

In step a), the bone screw can be screwed into the first bone fragment through a receiving opening of the bone plate. Said receiving opening can comprise the engagement and blocking contours according to the invention. It can also be, however, a receiving opening which has been disclosed in the prior art, for example one as described in WO 2004/086990 A1 or a purely cylindrical one.

As an option, the method can also include the following further step:
 d) blocking the second bone screw in the blocking contour.

Figure 1A:
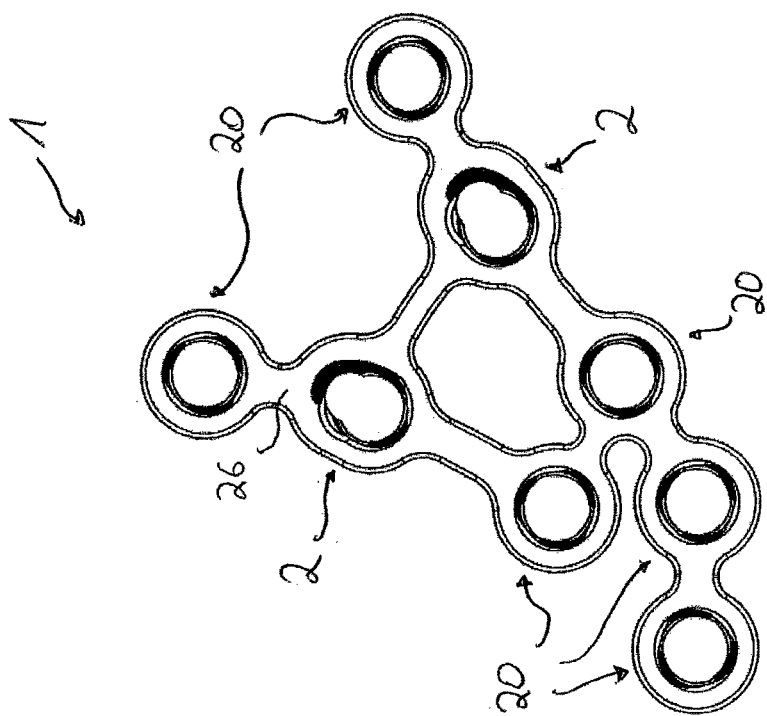
Figure 2B:
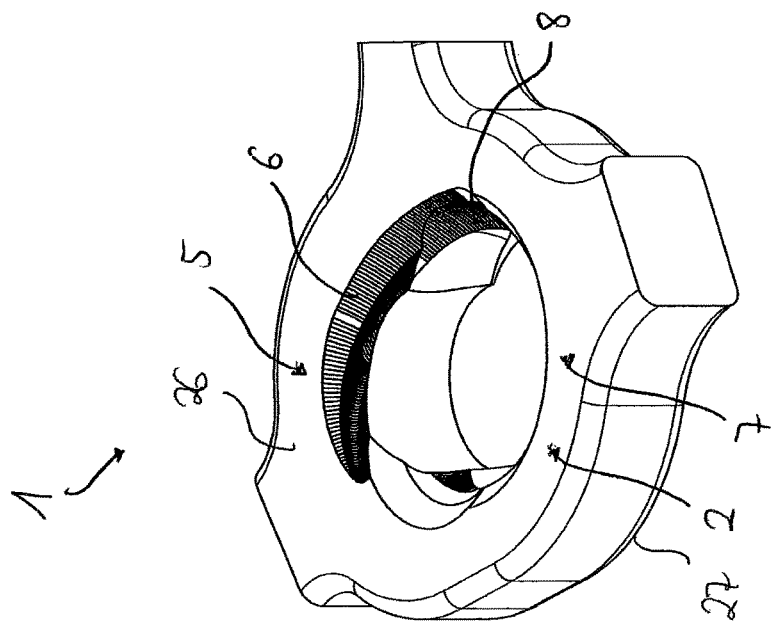
Figure 2A:
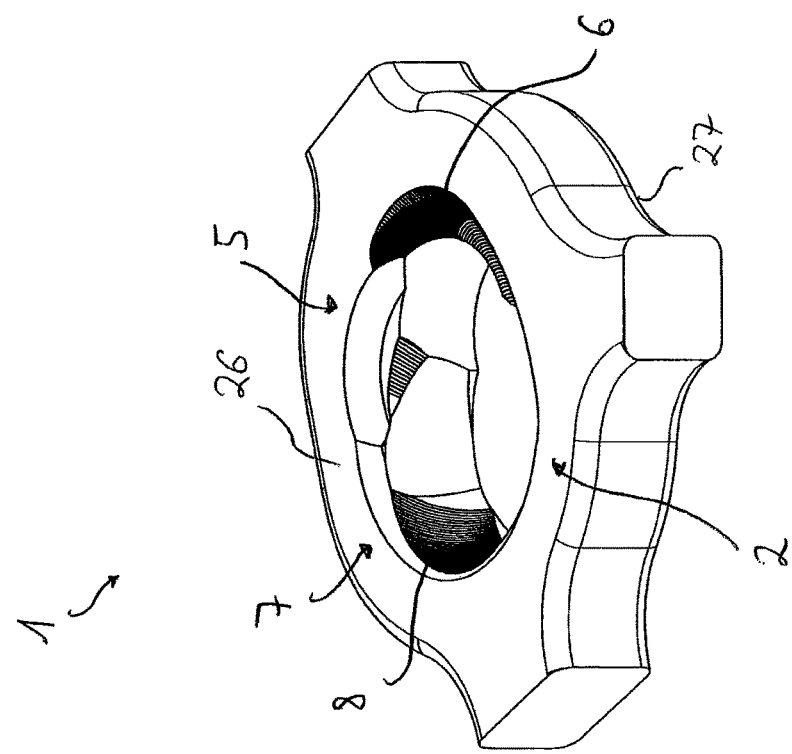
Figure 5B:
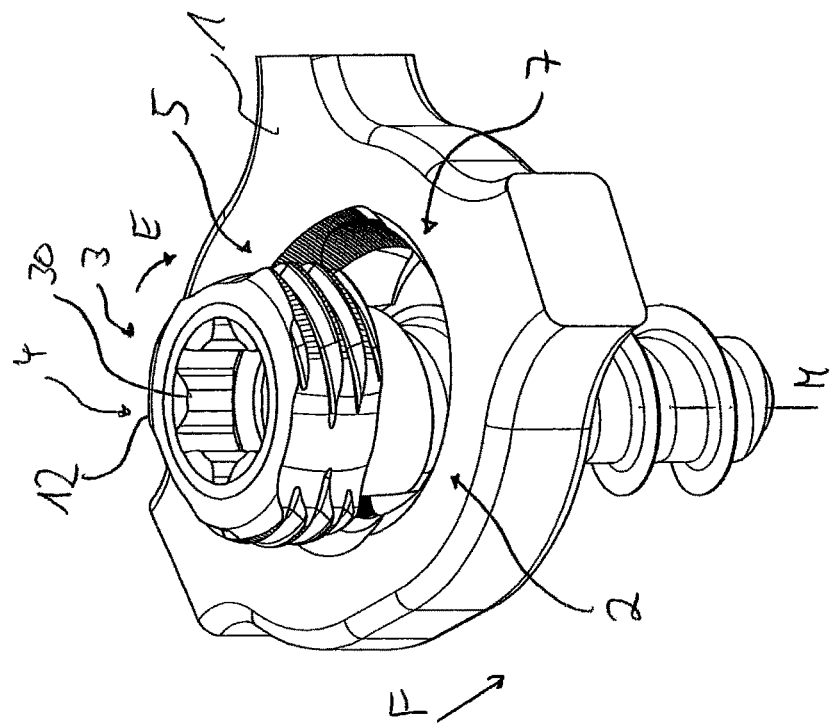
Figure 5A:
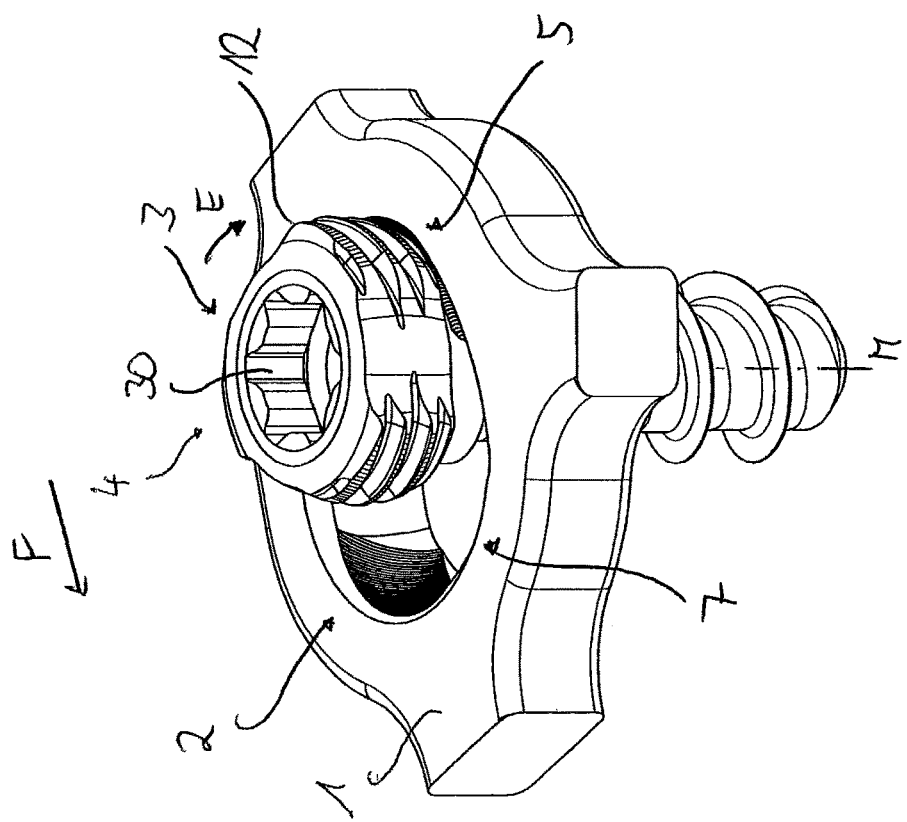
Figure 7A:
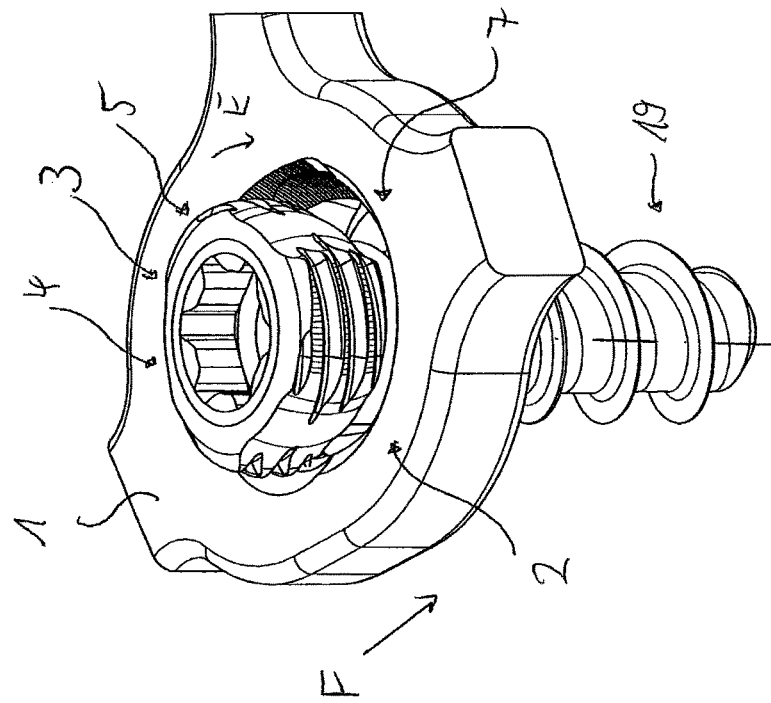
Figure 7B:
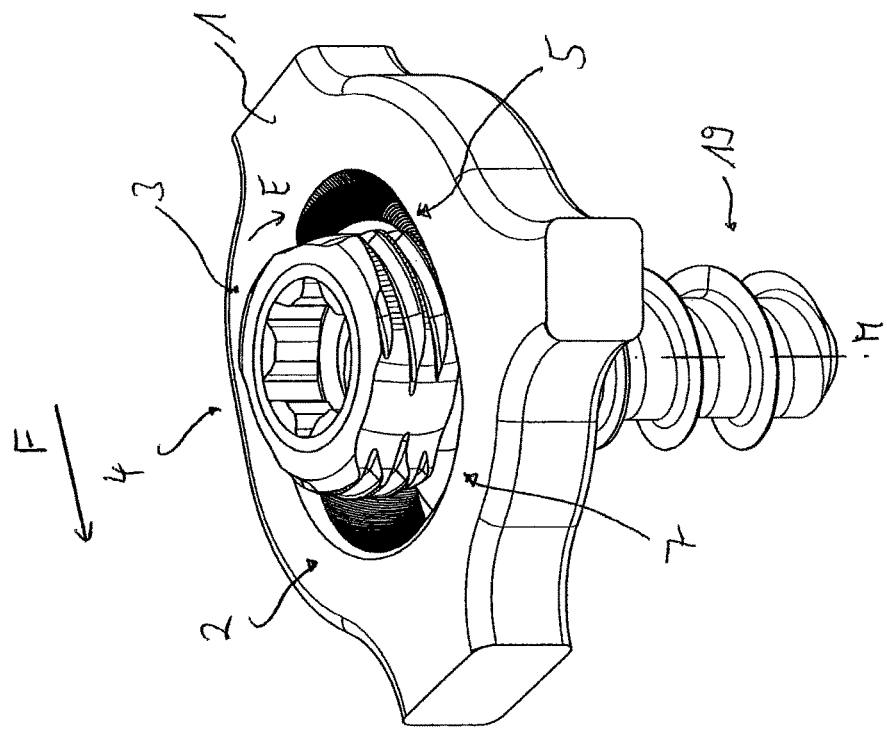
Figure 9B:
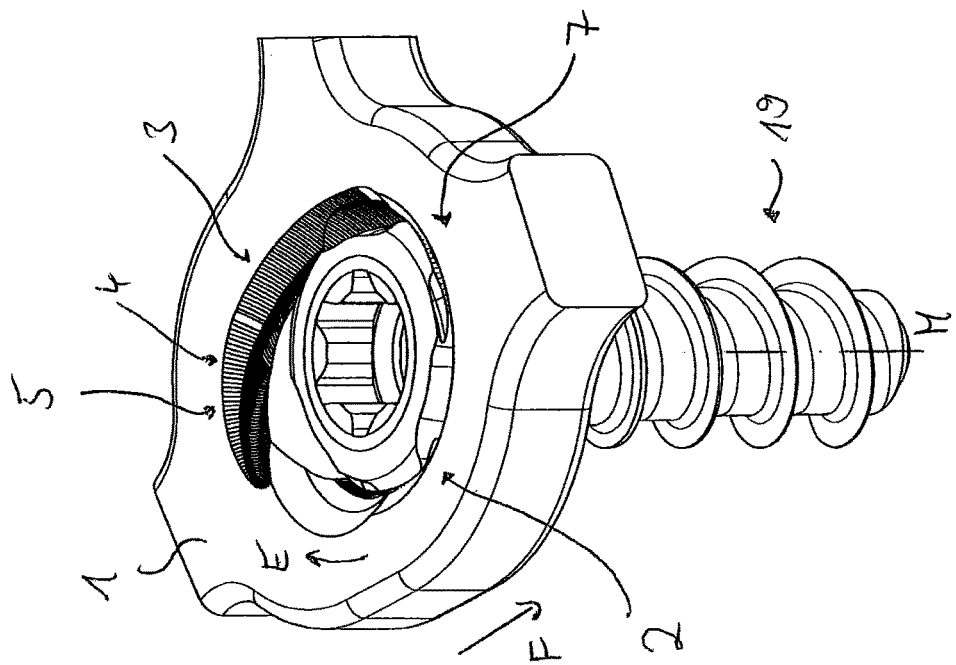
Figure 9A:
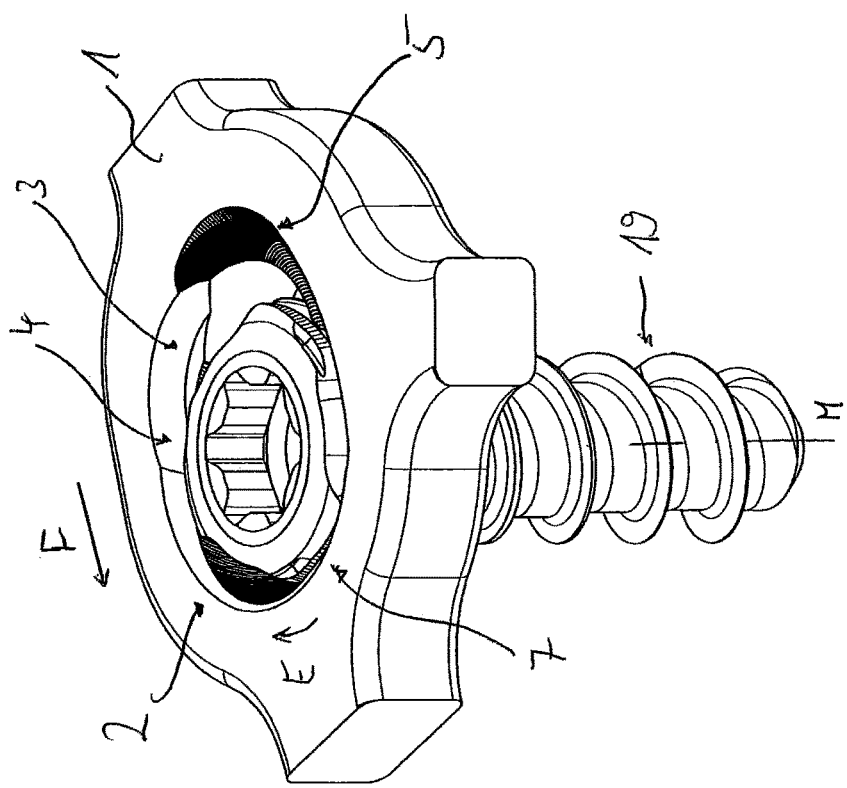

The invention is explained below by way of an exemplary embodiment and several drawings, in which:

FIG. 1a: shows a top view of a bone plate according to the invention in the form of a condyle plate;

FIG. 1b: shows a perspective view of the bone plate according to FIG. 1a;

FIG. 2a: shows a first perspective view of a view of a detail of one of the receiving openings of the bone plate;

FIG. 2b: shows a second perspective view of the view of the detail according to FIG. 2a;

FIG. 3a shows a top view of the view of the detail according to the FIGS. 2a and b;

FIG. 3b: shows a sectioned view along the line C-C in FIG. 3a;

FIG. 3c: shows a sectioned view along the line D-D in FIG. 3a;

FIG. 4a: shows a perspective view of a bone screw;

FIG. 4b: shows a top view of the bone screw according to FIG. 4a;

FIG. 5a: shows a first perspective view of the view of the detail according to FIG. 2a with a bone screw according to FIGS. 4a and b inserted in a compression region of the receiving opening;

FIG. 5b: shows a second perspective view of the view of the detail according to FIG. 5a;

FIG. 6a: shows a top view of the view of the detail according to the FIGS. 5a and b;

FIG. 6b: shows a sectioned view along the line E-E in FIG. 6a (the bone screw, however, not being shown in a sectioned manner);

FIG. 6c: shows a sectioned view along the line F-F in FIG. 6a (the bone screw, however, not being shown in a sectioned manner);

FIG. 7a: shows a first perspective view of the view of the detail according to FIG. 2a with the bone screw in the transition region between the compression region and the blocking region;

FIG. 7b: shows a second perspective view of the view of the detail according to FIG. 7a;

FIG. 8a: shows a top view of the view of the detail according to the FIGS. 7a and b;

FIG. 8b: shows a sectioned view along the line G-G in FIG. 8a (the bone screw, however, not being shown in a sectioned manner);

FIG. 8c: shows a sectioned view along the line H-H in FIG. 8a (the bone screw, however, not being shown in a sectioned manner);

FIG. 9a: shows a first perspective view of the view of the detail according to FIG. 2a with the bone screw in the blocking region;

FIG. 9b: shows a second perspective view of the view of the detail according to FIG. 9a;

FIG. 10a: shows a top view of the view of the detail according to the FIGS. 9a and b;

FIG. 10b: shows a sectioned view along the line I-I in FIG. 10a (the bone screw, however, not being shown in a sectioned manner);

FIG. 10c: shows a sectioned view along the line J-J in FIG. 10a (the bone screw, however, not being shown in a sectioned manner).

FIGS. 1a and 1b show two views of a bone plate 1 which is realized as a condyle plate. It includes a top surface 26, a bottom surface 27 which extends parallel to said top surface and two receiving openings 2 according to the invention, which are described further below in detail, and six receiving openings 20 not according to the invention which all extend from the top surface 26 to the bottom surface 27. The receiving openings 20 not according to the invention can comprise, for example, a blocking contour as disclosed in WO 2004/086990 A1.

FIGS. 2a, 2b and 3a to 3c show two different perspective views, one top view and two sectioned views, of one of the two receiving openings 2 which can be seen in FIG. 1. The receiving opening 2 includes a compression region 5 with a compression contour which is realized as an engagement contour 6 and a blocking region 7 with a blocking contour 8. The compression region 5 and the blocking region 7 each comprise a circular silhouette, said two circular silhouettes penetrating one another. A main axis K of the compression region 5 extends through the middle point of the circular silhouette of the compression region 5 and perpendicular to the top surface 26 of the bone plate 1. The compression region is delimited in part by a cylindrical wall portion 24. A main axis L of the blocking region 7 extends through the middle point of the circular silhouette of the blocking region 7 and also perpendicular to the top surface 26 of the bone plate 1. In the exemplary embodiment shown, the main axis K of the compression region 5 and the main axis L of the blocking region 7 are at a distance from one another of d=1 mm.

The engagement contour 6 comprises a cycloid-like guiding surface 10. A side wall 23, which extends at an angle, is formed between the guiding surface 10 and a top surface 26 of the bone plate 1. The engagement contour 6 additionally includes a rolling region 13 which includes a bottom surface 21, which extends parallel to the top surface 26, and a side surface 22 which extends between the top surface 26 and the bottom surface 21.

In addition, the engagement contour 6 comprises two projections 14, 14' which extend in a radial direction R. The radial direction R is to be understood, in this case, with reference to the main axis K of the compression region 5. The first projection 14 is arranged between the guiding surface 10 and the rolling region 13—more precisely: at the contact point between the top surface 26 of the bone plate 1, the guiding surface 10 and the side surface 22 of the rolling region 13. The second projection 14' is arranged between the rolling region 13 and the blocking contour 8—more precisely: at the contact point between the bottom surface 21 of the rolling region 13, the cylindrical wall portion 24 and one of the three recesses 16 which are explained again below.

The blocking contour 8 comprises three recesses 16, of which two are interrupted by the compression region 5. The three recesses 16 widen outward in a wedge-shaped manner away from a main axis L of the blocking region 7. In the region of said recesses 16, each blocking contour 8 is realized in a spherical manner. As an alternative to this, however, the recesses 16 can also be realized, for example, in a paraboloid, ellipsoid or hyperboloid manner. The recesses 16 are additionally arranged such that they extend around in a direction perpendicular to the main axis L of the blocking region 7. In the region of the recesses 16, the blocking contour 8 is described in an azimuth plane A, which extends perpendicularly to the main axis L of the blocking region 7, in each case by a root function, that is to say a function of the type $r=a_1+b_1\sqrt{\alpha}$, wherein r is the respective distance between the blocking contour 8 and the main axis L of the blocking region 7, $a_1$ and $b_1$ are constants and $\alpha$ stands for the respective circumferential angle. The azimuth plane A corresponds to the drawing planes of FIG. 3a.

A lead-out contour 25, which serves for guiding-out a bone screw in order to be able to remove it again in an easier manner out of the receiving opening 2, connects in each case to each of the three recesses 16. A countersink 28, which can serve for receiving a screw head with a spherical head bottom surface, is additionally present.

A cylindrical milling cutter, by way of which the silhouette of the compression region 5 is produced, can be used initially in a first step to produce the receiving opening 2. The cylindrical wall portion 24 originates from said first step. The further contours of the receiving opening 2 can then be produced in a second step by means of a milling cutter as disclosed in WO 2004/086990 A1 which includes a convex milling head with an at least approximately spherical contour.

FIGS. 4a and 4b show a bone screw 3 which can be inserted at a variable angle in each of the receiving openings 2, 20 of the bone screw 1. Said bone screw 3 is identical to the one disclosed in WO 2004/086990. It comprises a shank 19 with a thread 29 as well as a screw head 4 which protrudes outward beyond the shank 19 and the thread 29. The screw head 4 comprises an engagement contour 30 into which, for example, a screwdriver can be inserted in order to screw-in or unscrew the bone screw 3. In addition, the screw head 4 is provided with a circumferential outside surface 17 which extends substantially in the direction of a longitudinal axis M of the bone screw 3 and comprises three blocking projections 12, 12', 12" which are distributed uniformly in the circumferential direction, extend in the radial direction and have respective clamping surfaces 18. Recesses 15, 15', 15" are formed in each case between the blocking projections 12, 12', 12".

When viewed in an azimuth plane perpendicular to the longitudinal axis M (drawing plane of FIG. 4b), the clamping surfaces 18 widen outward in a wedge-shaped manner and away from the longitudinal axis M. The outside surface 17 is realized in a spherical manner in the region of the clamping surfaces 18.

On the one hand, the blocking projections 12, 12', 12" and the recesses 15, 15', 15" which are formed in between said blocking projections form a counter contour 9 which, together with the engagement contour 6 of the bone plate 1, can bring about a lateral movement of the bone screw 3. On the other hand, said clamping surfaces 18 make it possible to be able to block the screw head 4 with the blocking contour 8, at different angles relative to the bone plate, as is described in detail in WO 2004/086990 A1 (which, however, only discloses one receiving opening without the compression region according to the invention).

To fix the bone plate 1 to two bone fragments to be joined, the bone plate 1 is initially fixed to a first bone fragment, which is not shown here, by placing a bone screw through one of the plate holes 20 in FIGS. 1*a*/*b*, in a step a) which is not shown here. In a subsequent step b), a second bone screw 3 is inserted through the compression region 5 of the receiving opening 2 into the second bone fragment. At this point, the bone screw 3 and the receiving opening 2 assume the relative positions shown in FIGS. 5*a* to 6*c*. The shank 19 is screwed into the second bone fragment, which is not shown here for reasons of simplification. A bottom surface 11 of a first blocking projection 12 abuts against the guiding surface 10 and also against the side wall 23.

Step c) is then begun: By means of a screwdriver which engages in the engagement contour 30, the bone screw 3 is made to rotate in a screwing-in direction E. The bone screw 3 is moved as a result in the direction of its longitudinal axis M, and the shank 19 is driven further into the second bone fragment.

In this case, on the one hand the bottom surface 11 of the first blocking projection 12 slides down the cycloid-like guiding surface 10 and along the side wall 23. In order to make this possible, the pitch of the guiding surface 10 is matched to the bottom surface 11 of the blocking projection 12 and to the thread pitch of the shank 19. This already contributes to a lateral movement of the bone screw 3 in the direction of the blocking region 7, that is to say in the lateral direction F. The bone plate 1 is consequently moved counter to the lateral direction F relative to the second bone fragment to which the second bone screw 3 is fastened.

According to the invention, said lateral movement is additionally generated, however, by an engagement between the engagement contour 6 and the counter contour 9 on the screw head 4: During the transition into the position shown in FIGS. 7*a* to 8*c*, the second blocking projection 12' is rolled on the side surface 22 of the rolling region 13. For this purpose, the side surface 22 of the rolling region 13 is correspondingly matched to the blocking projection 12' and to the thread pitch of the shank 19.

If the bone screw 3 is then screwed even further in its screwing-in direction E, it is pulled even further into the second bone fragment. Finally, the bone screw 3 passes into the position shown in FIGS. 9*a* to 10*c* in which it is situated in the blocking region 8 of the receiving opening 2. As a result of rotating the bone screw 3 further in the screwing-in direction E, blocking can be achieved in a step d) between the blocking projections 12 and the recesses 16 of the blocking contour 8, as is described in detail in WO 2004/086990 A1 (which, however, only discloses one receiving opening without the compression region according to the invention).

The invention claimed is:

1. A bone plate with at least one receiving opening for a bone screw with a screw head,
   wherein the receiving opening includes a compression region with a compression contour and a blocking region with a blocking contour,
   the compression contour is realized and arranged in such a manner that rotation of the bone screw in a screwing-in direction brings about a lateral movement of the bone screw in the direction of the blocking region,
   the compression contour is realized as an engagement contour such that lateral movement is generatable, at least in part, by engagement between the engagement contour and a counter contour of the screw head, and
   the blocking contour is realized in such a manner that the bone screw is blockable, at various angles, relative to the bone plate,
   wherein the blocking contour has at least one recess which is arranged such that the at least one recess extends around in a direction perpendicular to the main axis of the blocking region.

2. The bone plate according to claim 1, wherein the lateral movement is generatable at least in part by rolling the screw head along the engagement contour.

3. The bone plate according to claim 1, wherein the engagement contour comprises at least one guiding surface, along which a bottom surface of the screw head is guidable, during rotation of the bone screw in its screwing-in direction.

4. The bone plate according to claim 3, wherein during rotation of the bone screw in its screwing-in direction, a bottom surface of a blocking projection which is arranged radially on the screw head is guidable along the at least one guiding surface.

5. The bone plate according to claim 1, wherein the engagement contour comprises at least one rolling region on which a blocking projection, which is arranged radially on the screw head, is rollable during at least part of the lateral movement.

6. The bone plate according to claim 5, wherein the rolling region includes a bottom surface and a side surface, which extends between a top surface and the bottom surface, and the blocking projection, which is arranged radially on the screw head, is rollable on said side surface during at least part of the lateral movement.

7. The bone plate according to claim 1, wherein the blocking contour comprises at least one recess which widens outward in a wedge-shaped manner away from a main axis of the blocking region in order to be able to receive and block a blocking projection which is arranged radially on the screw head.

8. The bone plate according to claim 7, wherein the blocking contour comprises at least two recesses which widens outward, in each case, in a wedge-shaped manner away from the main axis of the blocking region.

9. The bone plate according to claim 5, wherein the counter contour is formed by at least one blocking projection and/or at least one recess which are arranged between at least two blocking projections.

10. A surgical kit comprising at least one bone plate, at least one bone screw with a screw head and the at least one bone plate having at least one receiving opening for the at least one bone screw,
    wherein the receiving opening includes a compression region with a compression contour and a blocking region with a blocking contour,
    the compression contour is realized and arranged in such a manner that rotation of the at least one bone screw in a screwing-in direction brings about a lateral movement of the at least one bone screw in the direction of the blocking region,
    the compression contour is realized as an engagement contour such that lateral movement is generatable, at least in part, by engagement between the engagement contour and a counter contour of the at least one screw head, and the blocking contour is realized in such a manner that the at least one bone screw is blockable, at various angles, relative to the at least one bone plate, wherein the screw head is provided with a blocking projection, which is arranged radially on the screw head and has a circumferential outside surface which extends substantially in the direction of a longitudinal axis of the bone screw and comprises at least one clamping surface which, when viewed in an azimuth plane perpendicular to the longitudinal axis, widens outward in a wedge-shaped manner away from the longitudinal axis in order to be able to block the screw head by way of the blocking contour.

11. The surgical kit according to claim 10, wherein the circumferential outside surface of the screw head comprises at least three clamping surfaces which are distributed equally along their circumference and widen outward, in each case, in a wedge-shaped manner away from the longitudinal axis of the bone screw.

12. The surgical kit according to claim 10, wherein the at least one bone plate is configured such that the engagement contour comprises at least one guiding surface, along which a bottom surface of the screw head is guidable, during rotation of the bone screw in its screwing-in direction and the guiding surface is matched to the bone screw in such a manner that the bottom surface of the screw head is guidable along the guiding surface during the screwing-in of the bone screw.

13. The surgical kit according to claim 12, wherein the guiding surface is matched to a bottom surface of the screw head and to a thread pitch of a shank of the bone screw in such a manner that a bottom surface of a blocking projection, which is arranged radially on the screw head, is guidable along the guiding surface during the screwing-in of the bone screw.

14. The surgical kit according to claim 10, wherein the at least one bone plate is configured such that the engagement contour comprises at least one rolling region on which a blocking projection, which is arranged radially on the screw head, is rollable during at least part of the lateral movement and the rolling region of said at least one bone plate is matched in such a manner to the bone screw that the screw head is rollable on the rolling region during the screwing-in of the bone screw.

15. The surgical kit according to claim 14, wherein the at least one bone plate is configured such that the rolling region includes a bottom surface and a side surface, which extends between a top surface and the bottom surface, the blocking projection, which is arranged radially on the screw head, is rollable on said side surface during at least part of the lateral movement, and the side surface of the rolling region of said at least one bone plate is matched in such a manner to a counter contour which is arranged on the screw head and to a thread pitch of a shank of the bone screw that the screw head is rollable on the side surface of the rolling region during the screwing-in of the bone screw.

16. A method for fixing a bone plate according to claim 1 to two bone fragments to be joined, the method including:
a) fixing the bone plate to a first bone fragment by a first bone screw, b) inserting a second bone screw with a screw head through the compression region of the receiving opening onto a second bone fragment, c) rotating the second bone screw in a screwing-in direction, as a result of which a lateral movement of the second bone screw is brought about in the direction of the blocking region and the lateral movement is generated, at least in part, by engagement between the engagement contour and a counter contour on the screw head.

17. The method according to claim 16, further including:
d) blocking the second bone screw in the blocking contour.

18. A bone plate with at least one receiving opening for a bone screw with a screw head, wherein the receiving opening includes a compression region with a compression contour and a blocking region with a blocking contour, the compression contour is realized and arranged in such a manner that rotation of the bone screw in a screwing-in direction brings about a lateral movement of the bone screw in the direction of the blocking region, the compression contour is realized as an engagement contour such that lateral movement is generatable, at least in part, by engagement between the engagement contour and a counter contour of the screw head, and the blocking contour is realized in such a manner that the bone screw is blockable, at various angles, relative to the bone plate, wherein the counter contour is formed by at least one blocking projection and/or at least one recess which are arranged between at least two blocking projections.

19. A surgical kit comprising a bone plate, at least one bone screw with a screw head and the bone plate having at least one receiving opening for the at least one bone screw, wherein the receiving opening includes a compression region with a compression contour and a blocking region with a blocking contour, the compression contour is realized and arranged in such a manner that rotation of the at least one bone screw in a screwing-in direction brings about a lateral movement of the at least one bone screw in the direction of the blocking region, the compression contour is realized as an engagement contour such that lateral movement is generatable, at least in part, by engagement between the engagement contour and a counter contour of the at least one screw head, and the blocking contour is realized in such a manner that the at least one bone screw is blockable, at various angles, relative to the bone plate, wherein the circumferential outside surface of the at least one screw head comprises at least three clamping surfaces which are distributed equally along their circumference and widen outward, in each case, in a wedge-shaped manner away from the longitudinal axis of the bone screw.

* * * * *